United States Patent [19]
Kludas et al.

[11] 3,991,184
[45] Nov. 9, 1976

[54] AGENT FOR THE CARE OF SKIN
[76] Inventors: Martin Kludas, Herthastrasse 22, 1000 Berlin 33; Günter Borchert, Pruhssstrasse 57, 1000 Berlin 42, both of Germany
[22] Filed: Dec. 27, 1974
[21] Appl. No.: 536,893

Related U.S. Application Data
[63] Continuation of Ser. No. 403,922, Oct. 5, 1973, abandoned, which is a continuation-in-part of Ser. No. 213,219, Dec. 28, 1971, abandoned.

[52] U.S. Cl. .................................. 424/177; 424/359
[51] Int. Cl.² ..................... A61K 37/00; A61K 7/48
[58] Field of Search ....................... 424/177, 95, 359

[56] References Cited
FOREIGN PATENTS OR APPLICATIONS
1,205,609  9/1970  United Kingdom ................. 424/177

OTHER PUBLICATIONS
Chem. Abst., vol. 74, 30657g, 1971.
Cotte et al., "Amer. Perfumer & Cosmetics," vol. 82, No. 4, p. 58.

*Primary Examiner*—Lewis Gotts
*Assistant Examiner*—Cary Owens
*Attorney, Agent, or Firm*—Haseltine, Lake & Waters

[57] ABSTRACT

For the care of skin there is contemplated the use of untreated, soluble collagen having an unchanged substantially non-crosslinked collagen structure and obtained by the direct extraction from the connective tissue of skin.

8 Claims, No Drawings

AGENT FOR THE CARE OF SKIN

This Application is a continuation of copending application Ser. No. 403,922 filed Oct. 5, 1973, which in turn is a continuation-in-part of application Ser. No. 213,219, filed Dec. 28, 1971 and now abandoned.

BACKGROUND OF THE INVENTION a. Field of the Invention

The invention relates to agents for the care of the skin which are distinguished by proven efficacy for their purpose.

b. Prior Art

In cosmetology there are employed finished products or active substances whose purpose is to produce a revitalizing or rejuvenating effect on the skin. The terms "revitalizing" or "rejuvenating" are used generally and the contention that a revitalizing effect is achieved is generally not supported by reproducible, pharmacological proof.

It is known from gerontological research (Bjorksten) that the process of aging of the skin takes place mainly at the connective tissue of the cutis. This corium (85% of the skin thickness located under the epidermis) consists substantially of three-dimensionally intertwined collagenous fibres the chemical units of which are mainly monoamino acids. In the useful fibers, there is principally soluble collagen. In aging skin, the soluble collagen becomes insoluble, inelastic and rigid and is accompanied by the formation of intermolecular and intramolecular crosslinkings. As the skin ages the proportion of insoluble collagen increases, at the expense of the soluble collagen; the aging skin loses its resilience and therewith its water absorptivity and swelling capability.

The physiological aging process in the skin i.e., increase in insoluble collagen due to increased crosslinking, has an influence on cosmetics of entirely decisive importance. The skin loses its elasticity and its ability to swell due to its reduced water-binding capacity. It is true that the diminution in respect of soluble collagen is a physiological process forming part of the aging process but, from the cosmetic viewpoint, it is extremely undesirable.

The natural aging process is further accelerated, due to the influence of light and in particular of the sun, especially skin which is exposed to the action of light (the face, the neck and the hands). Soluble collagen is rapidly lost in skin subjected to the action of light (Shuster and Bottons). This makes the loss of resilience especially obvious. The skin becomes "leathery" and acquires an increased quantity of creases and wrinkles, because the water-binding capacity has been lost.

German Pat. No. 1,194,098 discloses a cosmetic agent for improving the skin turgor containing, in the cosmetic base, 3 to 15% by weight of a gelatine obtained from collagen and having a thixotropic resistance of below approximately 80 g Bloom and viscosity below approximately 20 m P.

However, the agent is intended to serve for improving the elasticity of the skin, since the collagen has, due to the processing necessary for converting it to a gelatine of the type specified, lost its specific resilience-promoting properties. Thus, such hydrolyzates are unsuitable for rejuvenation of the skin. The denatured, aged collagens are not utilized by the organism.

SUMMARY OF THE INVENTION

It is an object of the invention to halt the loss of soluble collagen in the skin by use of an agent for the care of the skin or to compensate for the loss of soluble collagen, thereby accomplishing the result of increasing the resilience or elasticity of the skin.

It has been ascertained that, by the use of native (untreated) soluble collagen in an agent for the care of the skin, a noteworthy improvement in the elasticity of the skin is achieved.

The invention is directed to an agent for the care of the skin characterized by the presence of native, soluble collagen having an unchanged, substantially un-crosslinked structure and moreover having a molecular weight of 5,000–50,000.

Any agent for the care of the skin which does not change the structure of the collagen is suitable as a base.

The soluble, native collagen is obtained from young and/or embryonal animal skin, preferably calfskin, by direct extraction from the connective tissue. The extraction is effected in a weakly acid aqueous medium, between 315 and 4.5 pH, while adding an organic acid and an organic salt, at low temperatures and in gentle manner, so that the collagen structure remains unchanged.

According to the invention, the agent for the care of the skin comprises untreated soluble collagen having an unchanged, substantially un-crosslinked collagen structure. The agent is in the form of a cream or lotion or other suitable carrier and the collagen is present in an amount of 5–10%.

DESCRIPTION OF PREFERRED EMBODIMENTS

According to the invention, there is provided an agent for the care of skin on the basis of cream and liquid emulsions or aqueous and aqueous-alcoholic lotions. This agent includes a content of 3–20% of native soluble collagen having unchanged native, extensively un-crosslinked structure and having a molecular weight of 5,–50,000.

The collagen is obtained from young and embryonal animal skin and preferably calfskin.

The collagen is obtained by extraction in an aqueous weakly acid pH range of between 3.5 and 4.5 with organic acids such as lactic acid, acetic acid or citric acid and salts thereof being added. The salts may be for example; sodium salts, potassium salts or tri-ethanol amine salts. The temperature of the medium is about 4°–10° c.

Both the acids and salts are required in the reaction.

The following cream products are given according to the invention by way of example for care of the skin:

EXAMPLE 1

| a) | Lanette N (Cetyl Stearyl alcohol) | 10.0 % |
|---|---|---|
| | Cetiol V (Oleic acid decylic ester) | 10.0 % |
| | Adeps Lanae | 2.0 % |
| | Miglyol 812 (vegetable oil) | 5.0 % |
| | Phenonip (preservative) | 0.4 % |
| | Phenonip | 0.4 % |
| | Liquid Karion F (Sorbitol-70 % aqueous solution) | 5.0 % |
| | Soluble collagen | 5.0 % |

EXAMPLE 2

| | | |
|---|---|---|
| a) | Emulsan MD (glycerine-mono-distearate) | 6.0 % |
| | Eumulgin B₁ (fatty alcohol polyglycol ether) | 3.0 % |
| | Lanette C (cetyl alcohol) | 3.0 % |
| | Adeps lanae | 3.0 % |
| | Cetiol V | 8.0 % |
| | Miglyol 812 | 6.0 % |
| | Isopropylpalmitate | 10.0 % |
| | Phenonip | 0.4 % |
| b) | Distilled water | 43.7 % |
| | Phenonip | 0.4 % |
| | Veegum (Magnesium-aluminum-silicate) | 1.5 % |
| | Liquid Karion F | 5.0 % |
| | Soluble collagen | 10.0 % |

Numerous experiments both on animals and also on human skin showed a noteworthy increase in skin resilience or elasticity after treatment with the product according to the invention.

On determining the resistance to tearing of skin wounds in rats subjected to the influence of soluble collagen, it was found that in the case of test animals treated with soluble collagen, as compared with the control animals, after 14 days there was an increase in the tearing values of approximately 60% and after 28 days an increase thereof of approximately 80%.

Proof of the existence of the built-in soluble collagen in the skin was provided histologically. The histological findings agree satisfactorily with the results in respect of the tearing values. From the 7th day on, i.e., the day on which the first visible fibre neoplasm was observed, it is found that in the case of the animals treated with soluble collagen, there were increased tearing values and, analogous to the histological pattern, in every case a qualitative and quantitative improvement of fibre neoplasm as compred with the controls.

From these experiments performed on animals, it can be concluded that soluble collagen introduced into the skin is utilized by the skin fabric. In this way, proof of genuine skin revitalization has been experimentally provided.

The results obtained by experiments on animals were confirmed in analogous dermatological tests on human skin employing collagen-containing creams according to the invention, as follows:

1. With the aid of a short-wave elastometer and by vibration measurement, the consistency and elastic resistance of the skin was determined. After treating with a collagen-containing cream, the skin elasticity was found to be clearly increased.
2. In accordance with the resonance frequency method applied to living human skin, after application of a collagen-containing cream, clearly enhanced hydration of the skin was ascertained.

Cream or lotion substances with soluble collagen present in an amount between 5 and 10% were applied in an amount of 3 to 4 grams per day for a period of one month to various patients. At the end of the one month period, visible results were seen, in that wrinkles in the skin are completly eliminated or greatly reduced. The magnitude of change which is obtained is dependent on the age of the person. On younger people, there will usually be complete elimination of wrinkles whereas in older people the wrinkles are harder to completely eliminate, but will be at lest greatly reduced.

For a dosage of 3 to 4 grams per day, about 25 grams are needed per week. This can be increased with no ill effects to about 30 to 40 grams per week in the case of badly wrinkled skin.

The soluble collagen can be incorporated in the cream or lotion in an amount between 3 and 20% and the effects of the invention achieved, however, the concentration of 5–10% is preferred from a practical and efficacious point of view.

The following are non-limiting examples of an extractor process which can be emloyed in practicing the invention:

EXAMPLE I

| | | |
|---|---|---|
| 10 | kilograms | of young or embryonal calfskin |
| 40 | " | of distilled water |
| 0.5 | " | of acetic acid |
| 0.3 | " | of potassium acetate |
| 0.1 | " | of methyl paraben |

EXAMPLE II

| | | |
|---|---|---|
| 10 | kilograms | of young or embryonal calfskin |
| 40 | " | of water |
| 0.2 | " | of lactic acid |
| 0.3 | " | of triethylaminolactate |
| 0.1 | " | of methyl paraben |

The calfskin is cleared of fat and flesh and reduced to a paste. The organic acids and their salts and the antiseptic (methyl paraben) are dissolved in water. This solution is mixed with the paste of calfskin and allowed to stand for at least four weeks at an ambient temperature of 4°–10° C, during which period the mixture is stirred quite a number of times. Subsequently, the mixture is centrifuged for separating the solid matter from the liquid matter; and the liquid component resulting from the centrifuging operation constitutes the soluble collagen.

What is claimed is:

1. An agent for the care of the skin in the form of a cosmetic preparation, said agent comprising a content of 3-20 per cent of native soluble collagen having unchanged native, extensively non-crosslinked structure, said collagen being obtained from skin selected from the group consisting of young and embryonal animal skin by extraction in an aqueous acid in a pH range between 3.5 and 4.5 with an organic acid selected from the group consisting of lactic acid, acetic acid and citric acid and salts thereof selected from the group consisting of sodium salts, potassium salts and tri-ethanol amine salts and at a temperature of 4°–10° C.

2. An agent as claimed in claim 1 wherein the collagen is calfskin collagen.

3. An agent as claimed in claim 1 wherein the acid is acetic acid and the salt potassium acetate, the ratio of acid to salt being 5:3.

4. An agent as claimed in claim 1 wherein the acid is lactic acid and the salt triethanolactate, the ratio of acid to salt being 2:3.

5. A method of preparing an agent for increasing the resilience, water absorptivity and swelling capability of skin, said method comprising forming a composition of a carrier and 3–20% of untreated soluble collagen having an unchanged substantially non-crosslinked collagen structure, said collagen being obtained from skin selected from the group consisting of young and embryonal animal skin by extraction from the connective tissue in an acid aqueous medium in a pH range between 3.5 and 4.5 at a temperature of 4°–10° C with at least one organic acid selected from the group consisting of lactic, acetic and citric acid and a salt thereof.

6. A method as claimed in claim 5 wherein said salt is sodium, potassium or tri-ethanol amine salts of the acids.

7. A method as claimed in claim 5 wherein the acid is acetic acid and the salt potassium acetate, the ratio of acid to salt being 5:3.

8. A method as claimed in claim 5 wherein the acid is lactic acid and the salt triethanolactate, the ratio of acid to salt being 2:3.

* * * * *